US012711165B2

(12) United States Patent
Mahmood et al.

(10) Patent No.: US 12,711,165 B2
(45) Date of Patent: Aug. 18, 2026

(54) AI-DRIVEN NATURAL LANGUAGE CO-PILOT FOR PATHOLOGY

(71) Applicant: THE BRIGHAM AND WOMEN'S HOSPITAL, INC., Boston, MA (US)

(72) Inventors: Faisal Mahmood, Brookline, MA (US); Ming-Yang Lu, Cambridge, MA (US); Bowen Chen, Stoneham, MA (US); Richard Chen, Gaithersburg, MD (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 18/976,751

(22) Filed: Dec. 11, 2024

(65) Prior Publication Data

US 2025/0190465 A1 Jun. 12, 2025

Related U.S. Application Data

(60) Provisional application No. 63/608,671, filed on Dec. 11, 2023.

(51) Int. Cl.

| | |
|---|---|
| ***G06F 16/3329*** | (2025.01) |
| ***G06F 40/284*** | (2020.01) |
| ***G16H 50/20*** | (2018.01) |

(52) U.S. Cl.
CPC ...... *G06F 16/33295* (2025.01); *G06F 40/284* (2020.01); *G16H 50/20* (2018.01)

(58) Field of Classification Search
CPC .. G06F 16/33295; G06F 40/284; G16H 50/20
See application file for complete search history.

(56) References Cited

U.S. PATENT DOCUMENTS

| | | | | |
|---|---|---|---|---|
| 2022/0130499 | A1* | 4/2022 | Zhou | G06V 10/25 |
| 2023/0076903 | A1* | 3/2023 | Conjeti | G16H 10/60 |

(Continued)

FOREIGN PATENT DOCUMENTS

| | | | | |
|---|---|---|---|---|
| WO | WO2025030094 | * | 2/2025 | G06F 16/55 |

OTHER PUBLICATIONS

Thawkar et al., XrayGPT: Chest Radiographs Summarization using Large Medical Vision-Language Models, 2023, arXiv, whole document (Year: 2023).*

(Continued)

*Primary Examiner* — Sonia L Gay
(74) *Attorney, Agent, or Firm* — Tarolli, Sundheim, Covell & Tummino LLP

(57) ABSTRACT

Systems and methods are provided for providing natural language decision support for pathology. A lower-dimensionality representation of each of a set of received pathology image is generated and a first set of tokens is generated from the representations of the set of pathology images by projecting the lower-dimensionality representations of the received pathology images to a same dimension as an embedding space of a large language model for text tokens or through multimodal blocks added to the large language model such as cross-attention. The large language model is trained on an instruction dataset complied from a plurality of pathology-related sources. A second set of tokens associated with a natural language prompt is received at the large language model. A response is determined from the first set of tokens and the second set of tokens at the large language model.

20 Claims, 3 Drawing Sheets

(56) References Cited

U.S. PATENT DOCUMENTS

| | | | | |
|---|---|---|---|---|
| 2023/0386646 | A1* | 11/2023 | Tanwani | G06V 10/806 |
| 2024/0177838 | A1* | 5/2024 | Liu | G16H 50/70 |
| 2024/0354436 | A1* | 10/2024 | Mukherjee | G06F 16/3344 |
| 2024/0428937 | A1* | 12/2024 | Natarajan | G16H 50/20 |

OTHER PUBLICATIONS

Wang et al., Automated Radiographic Report Generation Purely on Transformer: A Multicriteria Supervised Approach, 2022, IEEE, whole document (Year: 2022).*

Tian et al., A A Two-Stage Deep Learning Strategy for Pneumothorax Classification, IEEE, 2021, whole document (Year: 2021).*

Zhang et al., Large-Scale Domain Specific Pretraining for Biomedical Vision—Language Processing, 2023, arXiv, whole document (Year: 2023).*

Pisula et al., Language models are good pathologists: using attention-based sequence reduction and text-pre-trained transformers for efficient WSi, 2023, arXiv, whole document (Year: 2023).*

Li, LLaVA-Med: Training a Large Language-and-Vision Assistant for Biomedicine in One Day, 2023, arXiV, whole document (Year: 2023).*

* cited by examiner

AI-DRIVEN NATURAL LANGUAGE CO-PILOT FOR PATHOLOGY

RELATED APPLICATIONS

This application claims priority to U.S. Provisional Application Ser. No. 63/608,671, filed on Dec. 11, 2023. This invention relates to clinical decision support systems, and more particularly, to a system for providing analysis and interpretation of pathology images.

TECHNICAL FIELD

This invention relates to clinical decision support systems, and more particularly, to a system for providing analysis and interpretation of pathology images.

BACKGROUND

The field of computational pathology has witnessed a remarkable transformation in recent years, propelled by the convergence of several key trends including increased availability and institutional adoption of digital slide scanning, rapid progress in artificial intelligence (AI) research, increasing accessibility of large datasets, and substantial high-performance computing resources. With varying degrees of success, researchers have leveraged deep learning to address a diverse range of tasks, including cancer subtyping and grading, metastasis detection, survival, and response-to-treatment prediction, tumor site of origin prediction, image search, mutation prediction, and biomarker screening. At the same time, general purpose vision encoder models, which are trained on vast datasets of unlabeled histopathology images and can serve as versatile task-agnostic model backbones, are paving the way for further improvements across many tasks in computational pathology, both in performance and label efficiency.

SUMMARY

In accordance with one example, a system provides natural language decision support for pathology. The system includes a processor and a non-transitory computer readable medium storing instructions executable by the processor. The machine-executable instructions include an encoder that receives a pathology image and generates a representation of the pathology image. Additional encoders may be used to encode other patient related data such as genomics, electronic medical records, etc. A multimodal projector generates a first set of tokens from the representation of one or more pathology images. A large language model is trained on an instruction dataset complied from a plurality of pathology-related sources, a given training sample within the instruction dataset comprising a set of one or multiple pathology images and text describing or answering specific queries pertaining to the images. The large language model receives a second set of tokens associated with a prompt and determines a response from the first set of tokens and the second set of tokens.

In accordance with another example, a method provides natural language decision support for pathology. A lower-dimensionality representation for each received pathology image is generated and a first set of tokens is generated from the representation of the set of pathology images by projecting the lower-dimensionality representation of the received pathology image to a same dimension as an embedding space of a large language model for text tokens. The large language model is trained on an instruction dataset complied from a plurality of pathology-related sources. A second set of tokens associated with a natural language prompt is received at the large language model. A response is determined from the first set of tokens and the second set of tokens at the large language model.

In accordance with a further example, a system provides natural language decision support for pathology. The system includes a processor and a non-transitory computer readable medium storing instructions executable by the processor. The machine-executable instructions include a vision encoder that receives a set of pathology images and generates a representation for each pathology image. A multimodal projector generates a set of first set of tokens from the representation of pathology images. A user interface receives a prompt from a user as natural language text, and a tokenizer generates a second set of tokens from the prompt. A large language model is trained on an instruction dataset complied from a plurality of pathology-related sources. Each training sample within the instruction dataset includes one or more pathology images and text describing or answering specific queries related to the images. The large language model receives the second set of tokens and determines a response from the first set of tokens and the second set of tokens. The user interface displays the response to the user at an associated display.

DEFINITIONS

A "pathology image," as used herein, is an image of tissue from a human body used for the diagnosis of disease. Non-exclusive examples of pathology images include hematoxylin and eosin stain images, other images acquired using histological stains, immunochemistry images, electron microscope images, cytology images, multiplex images, gross pathology images, radiological images, and any other complimentary images.

A "pathology-related source" is a block of text that describes a pathological finding, and can include educational articles, image captions, pathology case reports, and regions of interest extracted from analysis of whole slide imaging.

DETAILED DESCRIPTION

Despite advances in automated image analysis and machine learning generally, developments in computational pathology do not yet reflect the important roles of natural language in pathology, as a key to unlocking rich, diverse sources of accumulated human medical knowledge, as a potential signal for model supervision, and as a unified medium for facilitating intuitive interaction between powerful artificial intelligence (AI) models and end users. Notably, in general machine learning, representative works demonstrated that large-scale vision language representation learning can augment vision-only AI models with new capabilities including zero-shot image recognition and text-to-image retrieval. Depending on the architectural design and training data and objectives, visual language pretrained systems can also often be finetuned for tailored tasks ranging from visual question answering and image captioning to object detection and semantic segmentation. In computational pathology, a few works have shown promising zero-shot performance in select diagnostic and retrieval tasks, while other works also experimented with designing specialized models for biomedical visual question answering or captioning. However, these models are not yet ready to serve as interactive assistants for pathologists, researchers using pathology image data, or pathology trainees.

The systems and methods described herein provide a vision language interactive AI assistant for human pathology powered by a custom, finetuned multimodal large language model (MLLM). The MLLM-based vision language AI assistant can reason over both visual and natural language inputs. Specifically, compared to text-only large language models (LLMs), a multimodal large language model (MLLM) is trained to understand and respond to user instructions in the form of natural language queries that may additionally contain inputs from other modalities such as images. The support for multi-modality is of particular value for the domain of histopathology since examining and interpreting visual information in high resolution microscopic images (in conjunction with other clinical information) remains the cornerstone of the discipline and extends to many aspects of disease diagnosis and management in modern medicine.

Figure 1:
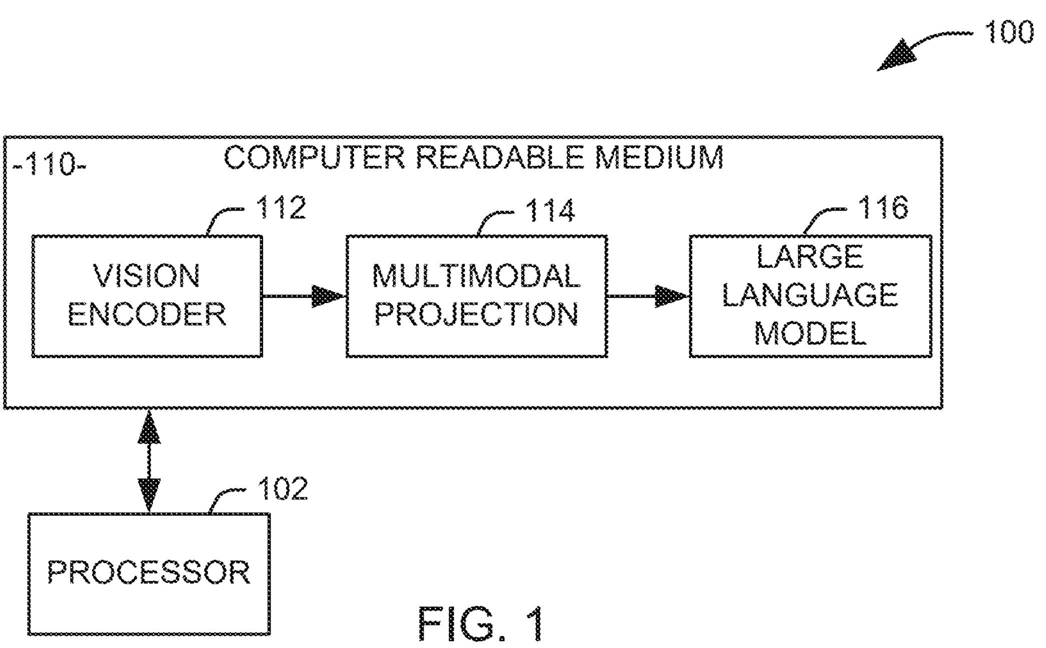
FIG. 1 illustrates one example of a multimodal large language model (MLLM) based vision language artificial intelligence (AI) assistant system for human pathology analysis.

FIG. 1 illustrates one example of a MLLM-based vision language AI assistant system 100 for human pathology analysis. The system 100 includes a processor 102 and a non-transitory computer readable medium 110 storing executable instructions, executed by the processor 102. It will be appreciated that the executable instructions can be spread across multiple non-transitory computer readable media that are operatively connected via an appropriate data connection, such that the executable instructions can be executed by multiple processors. In particular, the system 100 can be trained across multiple graphics processing units, with a number of graphics processing units and storage at the non-transitory computer readable medium 110 used for a given application be scalable with the application and the amount of available training data.

The executable instructions stored on the non-transitory computer readable medium 110 include a vision encoder 112 that converts a received image into a lower dimensionality representation of the image as a set of visual tokens. In one example, the vision encoder 112 can be implemented as an artificial neural network that is trained on a corpus of training images, such as a convolutional neural network or an autoencoder. Alternatively, one or more feature extraction algorithms can be used to reduce the image to a smaller set of numbers, such as a histogram of ordered gradients, a scale-invariant feature transformation, extraction of local binary patterns, extraction of frequency-based features, and similar algorithms. In one example, the vision encoder 112 can comprise a transformer encoder, trained on a corpus of histology images, that operates directly on patches of the image to assign one or more categorical parameters to the image. In one implementation, the vision encoder 112 can use an adaptation of the ViT-Large (ViT-L) architecture with twenty-four transformer multi-headed attention blocks, each with sixteen attention heads, an embedding dimension of 1,024 and a feed-forward hidden dimension of 4,096. The token size in this implementation is sixteen-by-sixteen, with learned absolute positional encoding added to each token. One example of an appropriate vision encoder 112 can be found in *Towards a general-purpose foundation model for computational pathology* by Chen et al., Nature Medicine (March 2024).

A multimodal projection model 114 that connects the outputs of the vision encoder 112 to a large language model 116 by projecting the visual tokens to a same dimension as an embedding space of the large language model for text tokens. For example, the multimodal projection model 114 can be implemented as a linear projector or a visual abstractor, such as Resampler or Q-Former. In one example, the multimodal projector model 114 includes an attention pooling layer followed by a two-layer multi-layer perceptron. The attention pooling layer uses a set of one hundred twenty-eight learned latent queries and multiheaded cross-attention to reduce a last layer feature map of the vision encoder 112 into a fixed length sequence of image tokens for increased training and inference efficiency, as well as to prevent the total sequence length of tokens from potentially exceeding the context window size of the large language model 116. In this example, the subsequent multi-layer perceptron includes a single hidden layer and Gaussian Error Linear Unit activation, projecting the image tokens up to the embedding dimension of the large language model. One example of an appropriate multiple modal projection model 114 can be found in *A Visual-Language Foundation Model for Computational Pathology* by Lu et al., Nature Medicine (March 2024).

The large language model 116 receives a set of text tokens representing a prompt and the tokens from the multimodal projection model 114 and predicts an appropriate response, which is decoded into natural language, for example, at a tokenizer. Specifically, the large language model 116 receives a set of tokens associated with a prompt along with the tokens from multimodal projection model 114 and determines a response from the two sets of tokens. The resulting text can be provided to a user via a user interface (not shown) or stored on a non-transitory computer readable medium, for example, as part of a record in an electronic health record database. In one implementation, the large language model 116 is implemented as a decoder-only transformer-based auto-regressive language model with forty transformer layers, each with forty attention heads, an embedding dimension of 5,120, a hidden dimension of 13,824 and rotary positional encodings, natively supporting a maximum context length of 4,096. The prompt can be provided by a user via the user interface or automatically generated, for example, to perform bulk processing of stored images or real-time analysis of received image. In these instances, a standard prompt or a set of tokens representing a standard prompt can be provided to the large language model 116 without user input.

In one example, the large language model 116 is trained on an instruction dataset complied from a plurality of pathology-related sources. Each training sample in the instruction dataset includes at least one pathology image and text describing or answering specific queries pertaining to the image or images. To ensure that the large language model 116 can generalize to a diverse range of instructions, the instruction data can include a number of different instruction formats, including open-ended multi-turn dialogue, detailed image descriptions, short-answer questions, multiple choice questions, object detection and segmentation masks, function calling and tool use for agentic workflows, and text-only questions. Instructions were derived from the various pathology-related sources, which included image captions, educational articles, pathology case reports, and regions of interest extracted from in-house whole-slide images. In one example, the instruction dataset can include around four hundred thousand instructions. It will be appreciated, however, that the system 100 can be scaled to utilize more or less training data, with hyperparameters of the model adjusted with the amount of available data, the available hardware, and the application.

Data filtering was performed for each source individually to ensure quality and relevance for training a pathology-specific vision language assistant. For example, image captions that are overly short (e.g., <twelve words) or uninformative and overly generic (e.g., "An H&E image of tumor") can be omitted. Captions or passages related to animal pathology, for example, text containing keywords related to animals such as "rat" or "pig" as well as experimental studies, identified as text containing appropriate keywords, such as "experimental" or "positive control.". In one implementation, this filtering is performed using regular expression pattern matching process. In addition, the instructions can include guardrail instruction examples, where the system is given image-specific instructions to avoid potential failure cases. For example, the large language model 116 can be trained to respond to a prompt such as "Describe this histology image of a lung mass" when no image is provided, with a response of "Sorry, I cannot assist you since you have not uploaded any image." Similarly, when given an image not related to pathology, the large language model 116 is trained to output "Sorry I can only assist you with queries related to pathology."

In one example, the large language model 116 is trained in concert with the multimodal projection model 114 in a two-stage process. In a first stage, the weights of the large language model 116 are kept frozen and only the multimodal projection model 114 receives parameter updates to learn a suitable projection from the space of image tokens from the vision encoder 112 to the shared embedding space of the text tokens used by the large language model. For this simple purpose, the system 100 is supervised to simply predict the caption corresponding to each image using a set of image-caption pairs without the need for curated instruction data. In one example, the first stage uses around a hundred thousand training samples. In a second stage both the large language model 116 and the multimodal projection model 114 are trained end-to-end to generate responses to diverse instructions that include both natural language and visual inputs, as described previously. Specifically, given an instruction $X_{instruct}$, a reference answer $X_{ans}$ and an image $X_{img}$, each represented as a sequence of tokenized inputs, the training process maximizes the likelihood, p, of each token in $X_{ans}$, indexed by i=1 to L, as an autoregressive language model given the parameters, $\theta_{projector}$ and $\theta_{llm}$, of the multimodal projection model 114 and the large language model 116, with an objective function expressed as:

$$L_{clm}(\theta_{projector}, \theta_{llm}) = \sum_{i=1}^{L} \log p\left(X_{ans,i} \mid X_{ans,1:i-1}, X_{instruct}, X_{img}; \theta_{projector}, \theta_{llm}\right)$$

This objective easily extends to multi-turn instruction data by conditioning on all previous turns of instruction and reference answer. For instructions where there is no image present, $X_{img}$ is not defined and is removed from the conditioning sequence. Similarly, if multiple images accompany a given instruction, their respective image tokens are interleaved with the text tokens according to their original position in the unprocessed input sequence, with a separator token such as the newline ("\n") token, may be inserted in-between consecutive images, and the full collection of image tokens are treated as $X_{img}$.

The system 100 significantly outperforms existing multimodal large language models for pathology queries. A study demonstrating this superior performance, as well as additional details for one implementation of the system, can be found in Appendix A of this application. The ability to understand and respond to complex queries in natural language in theory could enable the system 100 to serve as a helpful companion across various stages of human-in-the-loop clinical decision making, education, and research. For instance, in the clinic, the AI assistant might be able to ingest a histopathology image, provide an initial assessment of the morphological appearance, and identify potential features of malignancy. Further, the prompt can be expanded to include the results of additional testing and other relevant data to the system 100 to allow the system to make a final deduction to arrive at the diagnosis. In research, the system 100 can summarize the morphological features of large cohorts of histopathology images would potentially enable automated quantification and interpretation of morphological markers in large data cohorts or identify locations of disease in the pathology image and generate detection bounding boxes or segmentation masks. In medical education, the system 100 could help democratize access to expert level guidance and training in pathology, thereby narrowing the gap between regional disparities in healthcare provision.

Figure 2:
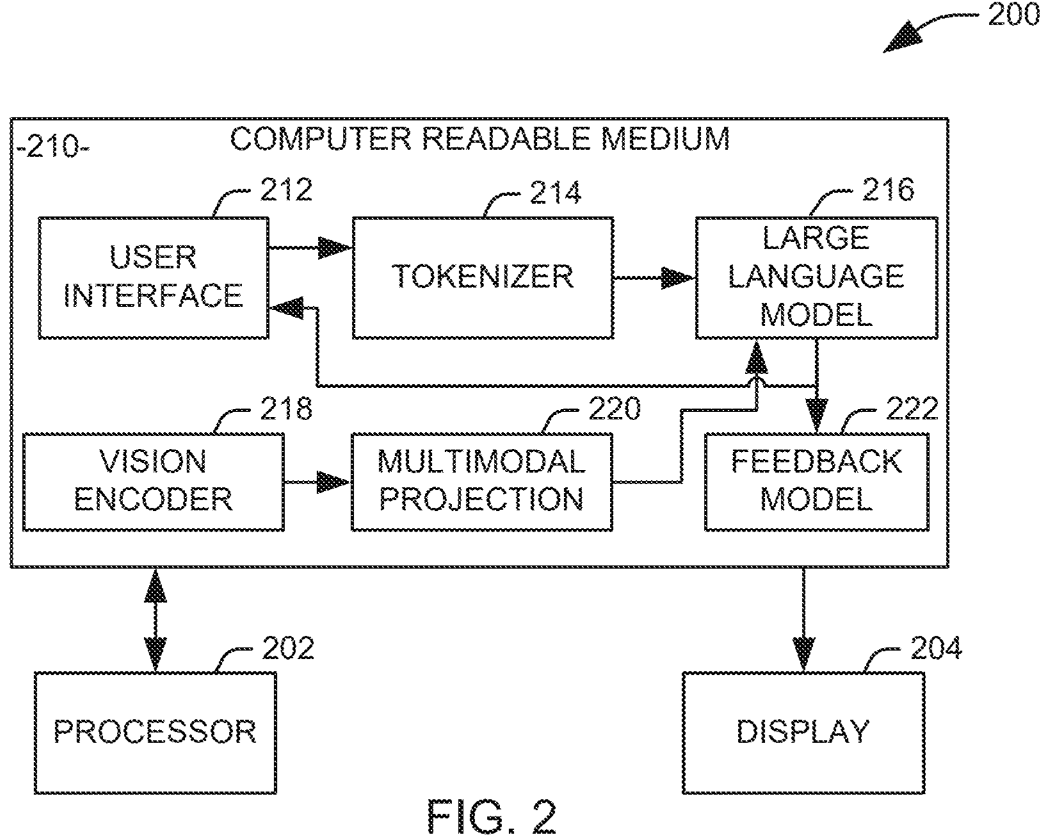
FIG. 2 illustrates another example of a MLLM-based vision language AI assistant system for human pathology analysis.

FIG. 2 illustrates another example of a MLLM-based vision language AI assistant system 200 for human pathology analysis. The system 200 includes a processor 202, a display 204, and a non-transitory computer readable medium 210 storing executable instructions that are executed by the processor 202. It will be appreciated that the executable instructions can be spread across multiple non-transitory computer readable media that are operatively connected via an appropriate data connection, such that the executable instructions can be executed by multiple processors.

The executable instructions include a user interface 212 that allows a user to enter a natural language prompt and, optionally, a pathology image. For example, the prompt can be a request to assess the image and identify potential features of malignancy or other disease with localization or a request for a diagnosis. Subsequently, the user could provide additional context about the underlying case, such as clinical parameters of the patient and the tissue site and ask the model to suggest a differential diagnosis request helpful suggestions for ancillary testing and immunohistochemical stains to narrow down a differential in the natural language prompt. The prompt from the user interface 212 is provided to a tokenizer 214 to reduce the text to tokens that are compatible with the embedding space of a large language model 216. The tokenizer 214 can use any appropriate tokenization technique including one or more of word-based tokenization, sub-word tokenization, or character-level tokenization. The user interface 212 can be provided at a local terminal, a remote terminal, or a portable device, such as a laptop, tablet, or mobile device.

Any pathology images provided with the prompt can be provided to a vision encoder 218 that generates a lower-dimensionality representation of each pathology image. In the illustrated implementation, the vision encoder 218 is implemented as an adaptation of the ViT-Large (ViT-L) architecture with twenty-four transformer multi-headed attention blocks, each with sixteen attention heads, an embedding dimension of 1,024 and a feed-forward hidden dimension of 4,096. The token size in this implementation is sixteen-by-sixteen, with learned absolute positional encoding added to each token.

A multimodal projector model 220 connects the outputs of the vision encoder 218 to the large language model 216 by projecting the visual tokens to a same dimension as an embedding space of the large language model 216 for text tokens. In the illustrated implementation, the multimodal projector model 220 includes an attention pooling layer followed by a two-layer multi-layer perceptron. The attention pooling layer uses a set of one hundred twenty-eight learned latent queries and multiheaded cross-attention to reduce a last layer feature map of the vision encoder 218 into a fixed length sequence of image tokens with an initial dimension of seven hundred sixty-eight for increased training and inference efficiency, as well as to prevent the total sequence length of tokens from potentially exceeding the context window size of the large language model. In this example, the subsequent multi-layer perceptron includes a single hidden layer and Gaussian Error Linear Unit activation, projecting the image tokens up to the embedding dimension of the large language model 216.

The large language model 216 generates an appropriate response to the prompt from the tokens provided from the multimodal projector model 220 and the tokenizer 214. The large language model is a transformer-based auto-regressive language model but may contain additional multimodal blocks such as cross-attention to enable it to incorporate tokenized representations from additional modalities such as images, in which case a separate multimodal projector is not required. In one example, the large language model 216 is implemented as a decoder-only transformer-based auto-regressive language model with forty transformer layers, each with forty attention heads, an embedding dimension on the order of five thousand, a hidden dimension of around thirteen thousand, and rotary positional encodings, natively supporting a maximum context length of 4,096. It will be appreciated, however, that these characteristics of the model 216 will vary among implementations. In another example, the large language model 216 is trained on a dataset of over 400,000 instructions to respond to pathology-specific queries. The dataset includes several different instruction formats, including open-ended multi-turn dialogue, detailed image descriptions, short-answer questions, multiple choice questions, object detection and segmentation, function calling and tool use for agentic workflows, and text-only questions. A diverse set of pathology-related sources are used to generate the instruction dataset, spanning image captions, educational articles, pathology case reports and regions of interests extracted from in-house whole slide images. Data filtering is performed for each source individually to ensure quality and relevance for training a pathology-specific vision language assistant, and various guiderails can be added to the training to provide appropriate responses to questions unrelated to pathology and potential error cases.

In one example, the large language model 216 is trained in concert with the multimodal projection model 220 in a two-stage process. In a first stage, the weights of the large language model 216 are kept frozen and only the multimodal projection model 220 receives parameter updates to learn a suitable projection from the space of image tokens from the vision encoder 218 to the shared embedding space of the text tokens used by the large language model 216. For this simple purpose, the system 200 is supervised to simply predict the caption corresponding to each image using a set of image-caption pairs without the need for curated instruction data. In one example, the first stage uses around a hundred thousand training samples.

In a second stage both the large language model 216 and the multimodal projection model 220 are trained end-to-end to generate responses to diverse instructions that include both natural language and visual inputs, using the instruction dataset described previously. Additional stages of training such as finetuning the model for targeted tasks (e.g. classification of pathology images from a specific disease model) and aligning its output with human preference via preference tuning, can also be performed to further steer the model's behavior.

The response generated at the large language model 216 is provided to the user at the display 204 via the user interface 212. In the illustrated implementation, the user is provided with a prompt at the user interface 212 to evaluate the response provided by the large language model 216. In one example, the user is prompted to rate the response as helpful or unhelpful. If a response is indicated to be helpful, the response, the prompt or the set of tokens representing the prompt, and any pathology images or set of tokens representing the pathology images, are provided to a feedback component 222. The feedback component 222 constructs a training instruction from the response, the prompt or the set of tokens representing the prompt, and any pathology images or set of tokens representing the pathology images. This training instruction can be used to provide further training to any or all of the vision encoder 218, the multimodal projector 220, and the large language model 216. In another example, the user is provided with multiple responses at the user interface 212 and asked to select among the provided responses. The response selected by the user can be passed to the feedback component 222 to generate a new training instruction.

In another example, the user may adapt the large language model 216 in a training-free manner to perform specific tasks using few-shot in-context examples. In the illustrated implementation, the user provides a task prompt and example data at the user interface 212 for the large language model 216, vision encoder 218, and multimodal projector 220. This task prompt can be a set of detailed instructions for the large language model 216 to follow in performing a specific task. The example data are pairs of example inputs that the large language model 216 and vision encoder 218 are expected to process for the user task and example outputs that the large language model 216 is expected to generate that follows the instructions of the user task. The example data can be labeled beforehand by the user or labeled in-place by the user in the user interface 212. Once the task prompt and example data is stored in the model, instead of the user needing to perform further training of large language model 216, vision encoder 218, and multimodal projector 220 for performing a specific task, the stored task prompt and example data are used in-context by the large language model 216 to perform the user's specific task in a training-free manner.

Figure 3:
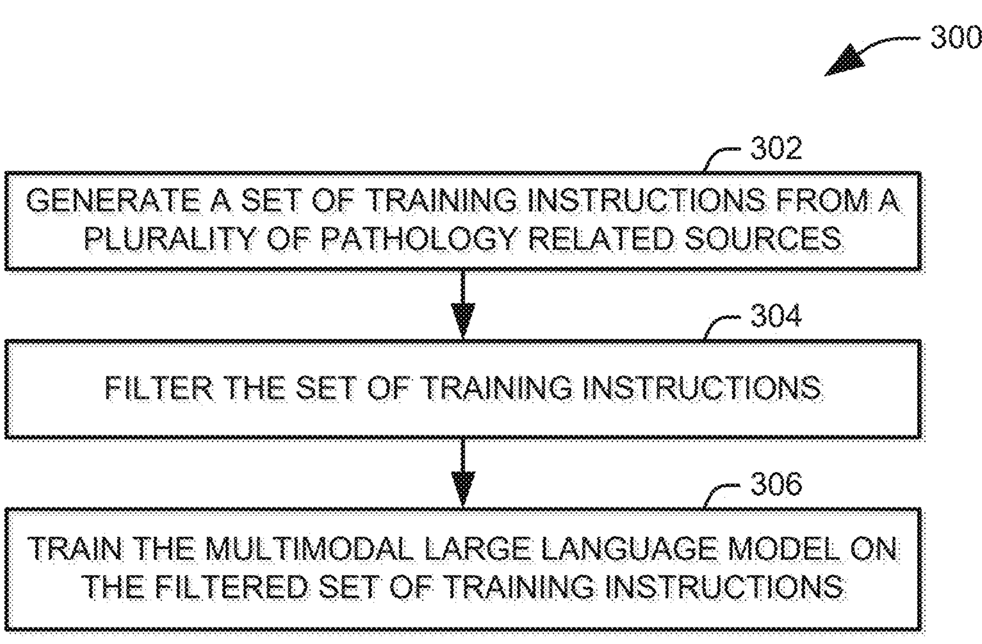
FIG. 3 illustrates one example of a method for training a multimodal large language model.
Figure 4:
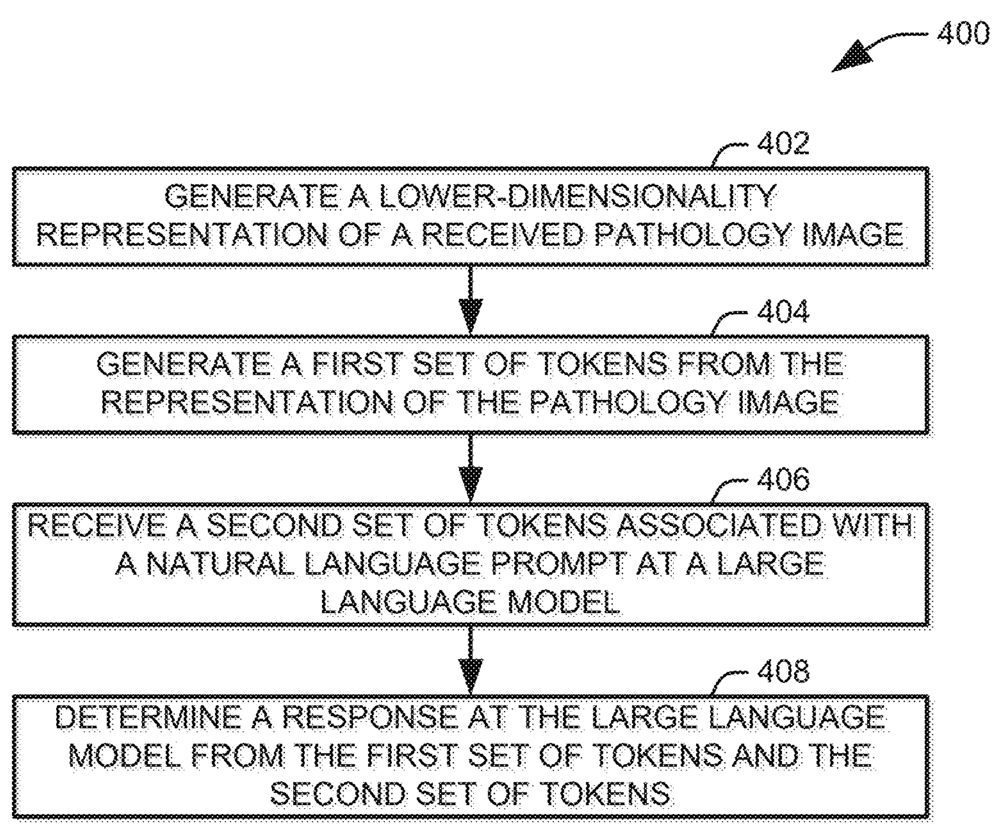
FIG. 4 illustrates an example of a method for providing natural language decision support for pathology.

In view of the foregoing structural and functional features described above, methods in accordance with various aspects of the present invention will be better appreciated with reference to FIGS. 3 and 4. While, for purposes of simplicity of explanation, the methods of FIGS. 3 and 4 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect the present invention.

FIG. 3 illustrates one example of a method 300 for training a multimodal large language model. At 302, a set of training instructions are generated from a plurality of pathology related sources. The training dataset can be selected to include any or all of open-ended multi-turn dialogue, detailed image descriptions, short-answer questions, multiple choice questions, object detection and segmentation masks, and text-only questions. The pathology-related sources can include, for example, image captions, educational articles, pathology case reports and regions of interests extracted from in-house whole slide images. At 304, the set of training instructions are filtered to ensure quality and relevance. For example, image captions that are overly short or uninformative and overly generic can be omitted. Captions or passages related to animal pathology or experimental studies can be identified via appropriate keywords and omitted, for example using a regular expression pattern matching process. At 306, the multimodal large language model is trained on the filtered set of training instructions. It will be appreciated that training can take place in multiple stages during which the parameters associated with one or more of the components of the multimodal large language model can be frozen, as to be unaffected by that stage of the training process.

FIG. 4 illustrates an example of a method 400 for providing natural language decision support for pathology. A lower-dimensionality representation of a received pathology image is generated at 402, and a first set of tokens is generated from the representation of the pathology image at 404 by projecting the lower-dimensionality representation of the received pathology image to a same dimension as an embedding space of a large language model for text tokens. It will be appreciated that multiple images can be associated with a given prompt, and when multiple images are received, a lower-dimensionality representation can be generated for each of the images, and the first set of tokens can be generated from the lower-dimensionality representations of all of the images.

In one example, the received pathology image is a whole slide image. In this example, the whole slide image is divided into a plurality of tiles, with each of the plurality of tiles having an associated location with the received pathology image. The whole slide image may additionally be segmented to locate a region of interest, which is also divided into a plurality of tiles corresponding to the received pathology image. The lower-dimensionality representation of the received pathology image includes a lower-dimensionality representation of each of the plurality of tiles, and the set of first set of tokens includes at least a subset of the first set of tokens generated from the lower-dimensionality representation of the plurality of tiles. This subset of the first set of tokens represents both the content of each tile and the associated location of the tile.

A second set of tokens associated with a natural language prompt is received at the large language model at 406. In one example, the natural language prompt is provided by a user via a user interface and the second set of tokens is generated from the prompt at a tokenizer associated with the user interface. A response is determined from the first set of tokens and the second set of tokens at the large language model at 408. The large language model is trained on an instruction dataset complied from a plurality of pathology-related sources. In one example, the plurality of pathology-related sources includes each of captions of medical images, educational articles, pathology case reports, and extracted regions from whole slide imaging. In one example, the user can provide feedback about the provided response via the user interface, with the feedback used to determine if a new instruction can be generated for the instruction dataset from the response, the prompt, and the pathology image.

Figure 5:
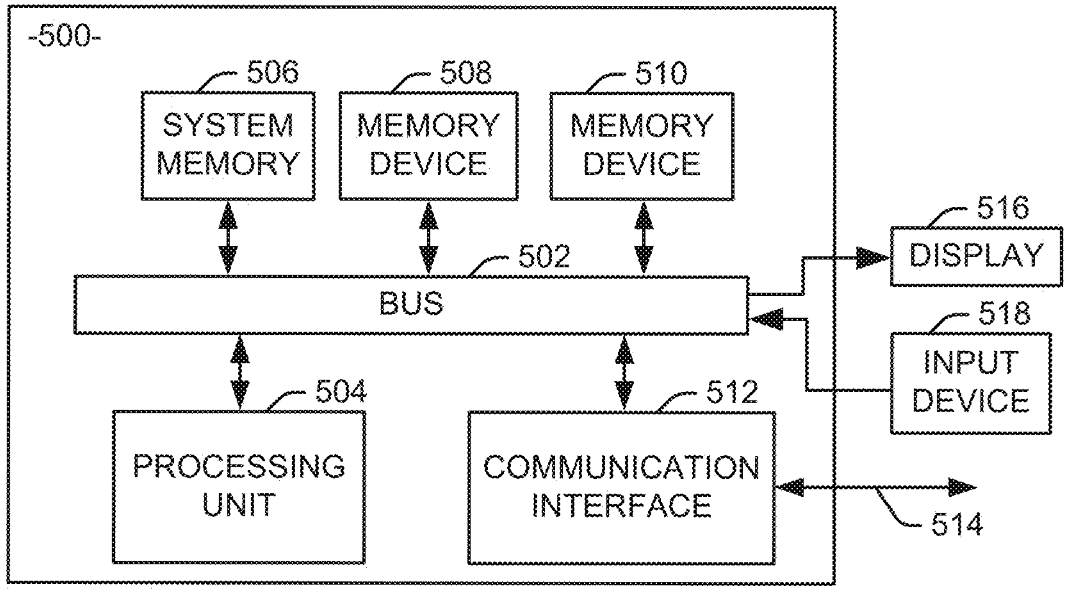
FIG. 5 is a schematic block diagram illustrating an exemplary system of hardware components capable of implementing examples of the systems and methods disclosed herein.

FIG. 5 is a schematic block diagram illustrating an exemplary system 500 of hardware components capable of implementing examples of the systems and methods disclosed herein. The system 500 can include various systems and subsystems. The system 500 can be a personal computer, a laptop computer, a workstation, a computer system, an appliance, an application-specific integrated circuit (ASIC), a server, a server BladeCenter, a server farm, etc.

The system 500 can include a system bus 502, a processing unit 504, a system memory 506, memory devices 508 and 510, a communication interface 512 (e.g., a network interface), a communication link 514, a display 516 (e.g., a video screen), and an input device 518 (e.g., a keyboard, touch screen, and/or a mouse). The system bus 502 can be in communication with the processing unit 504 and the system memory 506. The additional memory devices 508 and 510, such as a hard disk drive, server, standalone database, or other non-volatile memory, can also be in communication with the system bus 502. The system bus 502 interconnects the processing unit 504, the memory devices 506-510, the communication interface 512, the display 516, and the input device 518. In some examples, the system bus 502 also interconnects an additional port (not shown), such as a universal serial bus (USB) port.

The processing unit 504 can be a computing device and can include an application-specific integrated circuit (ASIC). The processing unit 504 executes a set of instructions to implement the operations of examples disclosed herein. The processing unit can include a processing core.

The additional memory devices 506, 508, and 510 can store data, programs, instructions, database queries in text or compiled form, and any other information that may be needed to operate a computer. The memories 506, 508 and 510 can be implemented as computer-readable media (integrated or removable), such as a memory card, disk drive, compact disk (CD), or server accessible over a network. In certain examples, the memories 506, 508 and 510 can include text, images, video, and/or audio, portions of which can be available in formats comprehensible to human beings.

Additionally or alternatively, the system 500 can access an external data source or query source through the communication interface 512, which can communicate with the system bus 502 and the communication link 514.

In operation, the system 500 can be used to implement one or more parts of a natural language system for analysis of pathology images. Computer executable logic for implementing the diagnostic system resides on one or more of the system memory 506, and the memory devices 508 and 510 in accordance with certain examples. The processing unit 504 executes one or more computer executable instructions originating from the system memory 506 and the memory devices 508 and 510. The term "computer readable medium" as used herein refers to a medium that participates in providing instructions to the processing unit 504 for execution. This medium may be distributed across multiple discrete assemblies all operatively connected to a common processor or set of related processors.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine-readable mediums for storing information. The term "machine-readable medium" includes, but is not limited to, portable or fixed storage devices, optical storage devices, wireless channels, and/or various other storage mediums capable of storing that contain or carry instruction(s) and/or data.

In the preceding description, specific details have been set forth in order to provide a thorough understanding of example implementations of the invention described in the disclosure. However, it will be apparent that various implementations may be practiced without these specific details. For example, circuits, systems, networks, processes, and other components may be shown as components in block diagram form in order not to obscure the example implementations in unnecessary detail. In other instances, well-known circuits, processes, algorithms, structures, and techniques may be shown without unnecessary detail in order to avoid obscuring the examples. The description of the example implementations will provide those skilled in the art with an enabling description for implementing an example of the invention, but it should be understood that various changes may be made in the function and arrangement of elements without departing from the spirit and scope of the invention. Accordingly, the present invention is intended to embrace all such alterations, modifications, and variations that fall within the scope of the appended claims.

What is claimed is:

1. A system for providing natural language decision support for pathology, the system comprising:

a processor; and a non-transitory computer readable medium storing instructions executable by the processor, the machine-executable instructions comprising:

a vision encoder that receives a pathology image and generates a representation of the pathology image;

a multimodal projector that generates a set of first set of tokens from the representation of the pathology image;

a user interface that receives a prompt from a user as natural language text;

a tokenizer that generates a second set of tokens from the prompt; and a large language model that is trained on an instruction dataset complied from a plurality of pathology-related sources, each training sample within the instruction dataset comprising a set of pathology images and text describing or answering specific queries pertaining to the images, the large language model receiving the second set of tokens and determining a response from the first set of tokens and the second set of tokens, the instruction dataset being selected as to exclude any text determined to be a generic description of an image;

wherein the user interface displays the response to the user at an associated display.

2. The system of claim 1, wherein the instruction dataset is selected as to exclude text associated with pathology images of animals, wherein text associated with pathology images of animals is identified via a regular expression pattern matching process using a set of key phrases.

3. The system of claim 1, wherein the response is a first response of a plurality of responses and the user interface allows the user to select a response from the plurality of responses, the image and the selected response being added to the instruction data set as a training sample.

4. The system of claim 1, wherein the response is a first response of a plurality of responses and the user interface allows the user to rate a response as one of helpful and unhelpful, the image and the selected response being added to the instruction data set as a training sample when the response is rated as helpful.

5. The system of claim 1, wherein the user interface allows the user to provide a task prompt and example data that are stored for training-free adaption to the user's task.

6. A system for providing natural language decision support for pathology, the system comprising:

a processor; and a non-transitory computer readable medium storing instructions executable by the processor, the machine-executable instructions comprising:

a vision encoder that receives a pathology image and generates a representation of the pathology image;

a multimodal projector that generates a set of first set of tokens from the representation of the pathology image;

a user interface that receives a prompt from a user as natural language text;

a tokenizer that generates a second set of tokens from the prompt; and a large language model that is trained on an instruction dataset complied from a plurality of pathology-related sources, each training sample within the instruction dataset comprising a set of pathology images and text describing or answering specific queries pertaining to the images, the large language model receiving the second set of tokens and determining a response from the first set of tokens and the second set of tokens, the instruction dataset being selected as to exclude text associated with pathology images of animals, wherein text associated with pathology images of animals are identified via a regular expression pattern matching process using a set of key phrases;

wherein the user interface displays the response to the user at an associated display.

7. A system for providing natural language decision support for pathology, the system comprising:

a processor; and a non-transitory computer readable medium storing instructions executable by the processor, the machine-executable instructions comprising:

a vision encoder that receives a pathology image and generates a representation of the pathology image;

a multimodal projector that generates a first set of tokens from the representation of the pathology image; and a large language model that is trained on an instruction dataset complied from a plurality of pathology-related sources, a given training sample within the instruction dataset comprising a set of pathology images and text describing or answering specific queries pertaining to the images, the large language model receiving a second set of tokens associated with a prompt and determining a response from the first set of tokens and the second set of tokens, the instruction dataset being selected as to exclude experimental studies, wherein experimental studies are identified via a regular expression pattern matching process using a set of key phrases.

8. The system of claim 7, wherein the response is a first response of a plurality of responses and the user interface allows the user to select a response from the plurality of responses, the image and the selected response being added to the instruction data set as a training sample.

9. The system of claim 7, wherein the response is a first response of a plurality of responses and the user interface allows the user to rate a response as one of helpful and unhelpful, the image and the selected response being added to the instruction data set as a training sample when the response is rated as helpful.

10. The system of claim 7, wherein one of the second set of tokens and the prompt are stored on the non-transitory computer readable medium, and the second set of tokens is provided to the large language model without input by a user.

11. The system of claim 7, further comprising an image segmenter that selects a region of interest within an image, the pathology images being a plurality of tiles generated from the region of interest and the first set of tokens representing the content and position of the pathology images.

12. The system of claim 7, wherein the plurality of pathology-related sources includes at least two of captions of medical images, educational articles, pathology case reports, and extracted regions from whole slide imaging.

13. The system of claim 1, wherein one of the second set of tokens and the prompt are stored on the non-transitory computer readable medium, and the second set of tokens is provided to the large language model without input by a user.

14. The system of claim 1, further comprising an image segmenter that selects a region of interest within an image, the pathology images being a plurality of tiles generated from the region of interest and the first set of tokens representing the content and position of the pathology images.

15. The system of claim 1, wherein the plurality of pathology-related sources includes at least two of captions of medical images, educational articles, pathology case reports, and extracted regions from whole slide imaging.

16. The system of claim 6, wherein the response is a first response of a plurality of responses and the user interface allows the user to select a response from the plurality of responses, the image and the selected response being added to the instruction data set as a training sample.

17. The system of claim 6, wherein the response is a first response of a plurality of responses and the user interface allows the user to rate a response as one of helpful and unhelpful, the image and the selected response being added to the instruction data set as a training sample when the response is rated as helpful.

18. The system of claim 6, wherein one of the second set of tokens and the prompt are stored on the non-transitory computer readable medium, and the second set of tokens is provided to the large language model without input by a user.

19. The system of claim 6, further comprising an image segmenter that selects a region of interest within an image, the pathology images being a plurality of tiles generated from the region of interest and the first set of tokens representing the content and position of the pathology images.

20. The system of claim 6, wherein the plurality of pathology-related sources includes at least two of captions of medical images, educational articles, pathology case reports, and extracted regions from whole slide imaging.

* * * * *